United States Patent

Nishiyama et al.

[11] Patent Number: 5,856,436
[45] Date of Patent: Jan. 5, 1999

[54] DEPSIPEPTIDE DERIVATIVE, PROCESS FOR PRODUCTION THEREOF, AND NOVEL INTERMEDIATE THEREFOR

[75] Inventors: Hitoshi Nishiyama, Neyagawa; Masaru Ohgaki, Kobe; Ryo Yamanishi, Mishima-gun, all of Japan

[73] Assignee: Fujisawa Pharmaceutical Co., Ltd., Osaka, Japan

[21] Appl. No.: 973,718

[22] PCT Filed: Jun. 24, 1996

[86] PCT No.: PCT/JP96/01748

§ 371 Date: Dec. 29, 1997

§ 102(e) Date: Dec. 29, 1997

[87] PCT Pub. No.: WO97/02256

PCT Pub. Date: Jan. 23, 1997

[30] Foreign Application Priority Data

Jun. 30, 1995 [JP] Japan ..................... 7-187889

[51] Int. Cl.$^6$ .............. A61K 38/12; C07K 7/00; C07K 16/00; C07K 17/00
[52] U.S. Cl. .................. 530/317; 514/9; 514/11
[58] Field of Search ............... 530/317; 514/9, 514/11

[56] References Cited

U.S. PATENT DOCUMENTS 5,514,773  5/1996  Nishiyama et al. ............ 530/317
5,646,244  7/1997  Nishiyama et al. ............ 530/317

FOREIGN PATENT DOCUMENTS 7-233068   9/1995   Japan.
93/19053   9/1995   WIPO.

*Primary Examiner*—Cecilia J. Tsang
*Assistant Examiner*—S. G. Marshall
*Attorney, Agent, or Firm*—Oblon, Spivak, McClelland, Maier & Neustadt, P.C.

[57] ABSTRACT

A novel industrial process for producing an anthelmintic depsipeptide derivative represented by structural formula (I), which is excellent in the yield etc.

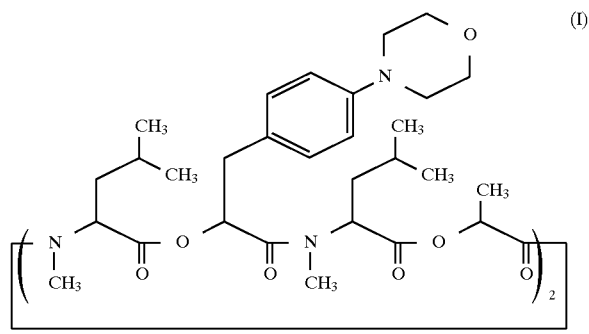

10 Claims, No Drawings

DEPSIPEPTIDE DERIVATIVE, PROCESS FOR PRODUCTION THEREOF, AND NOVEL INTERMEDIATE THEREFOR

This application is a 371 of PCT/JP96/01748, filed Jun. 24, 1996.

TECHNICAL FIELD

This invention relates to an alternative production technology for depsipeptide derivatives having anthelmintic activity and to novel intermediates for synthesis of such depsipeptides.

BACKGROUND ART

The following objective compound (I) is an anthelmintic compound known to have high parasiticidal activity and be suitable for human and animal use, and for its production there is known a process using the following route of total synthesis (WO 93/19053). The prior art route is:

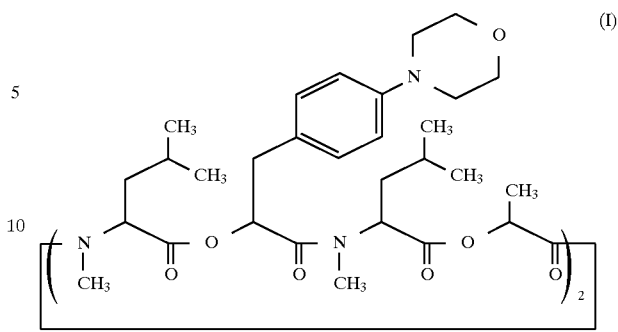

In accordance with this invention, the objective compound (I) or salt thereof can be produced by a process comprising the following series of steps.

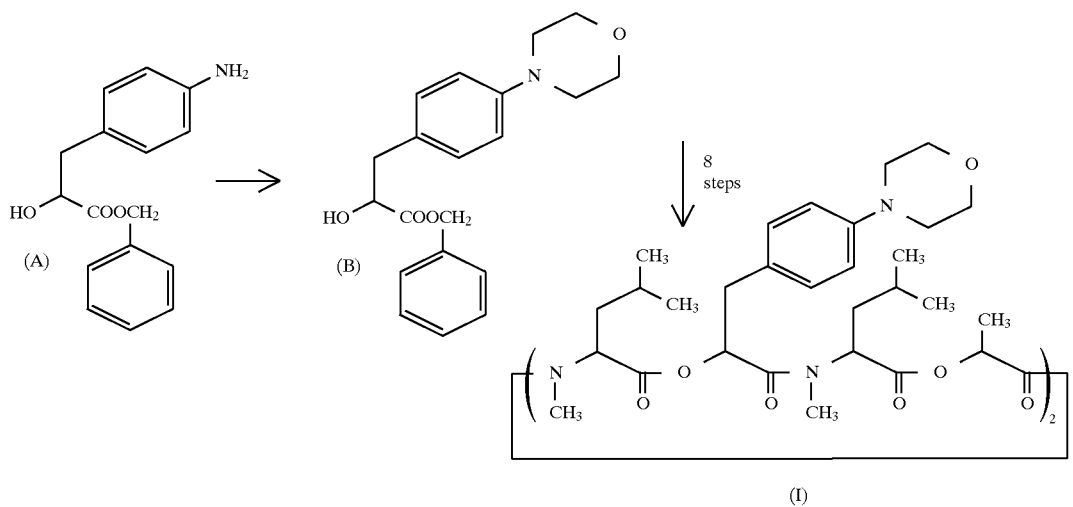

However, this process is not altogether suitable for industrial-scale production, for each of the intermediates in the route from compound (B) to objective compound (I) has the basic group morpholino which restricts handling and prevents recrystallization for purification, with the consequence that resort must be had to column chromatography or the like for purification.

Having been developed to overcome the above disadvantages, this invention provides a novel industrial process for producing the objective compound (I) in good yield by way of synthesis via novel intermediates.

DISCLOSURE OF INVENTION

The objective depsipeptide derivative of this invention is a known compound which may be represented by the following general formula (I).

Production schema
Step 1
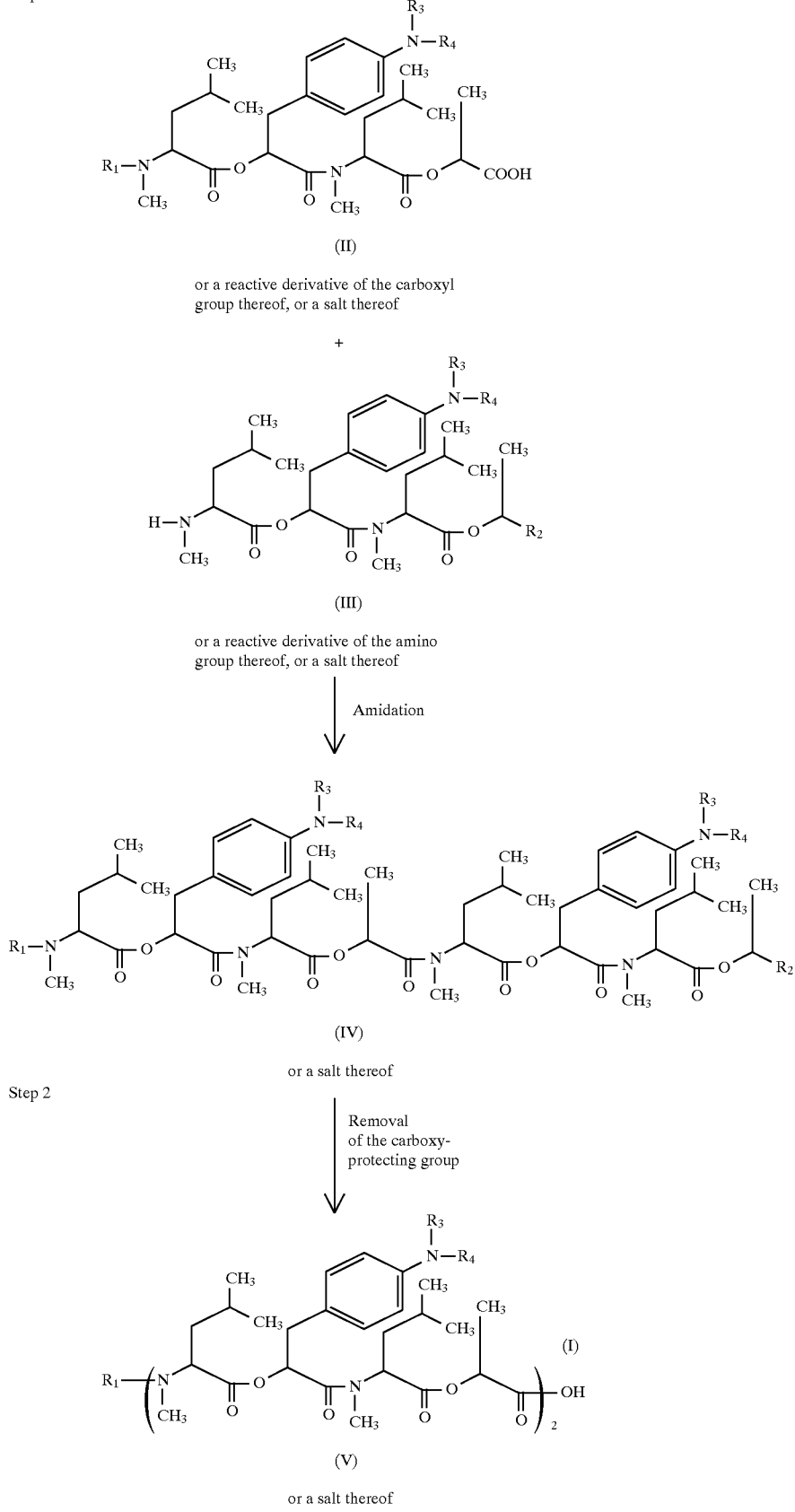
or a reactive derivative of the carboxyl
group thereof, or a salt thereof
+
or a reactive derivative of the amino
group thereof, or a salt thereof
Amidation
or a salt thereof
Step 2
Removal
of the carboxy-
protecting group
or a salt thereof Step 3
Removal of the carboxy-protecting group
↓
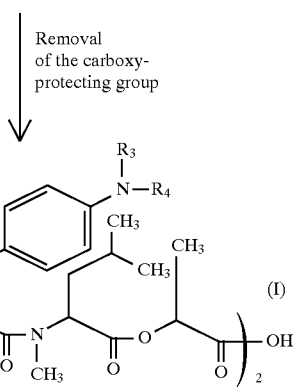
(VI)
or a salt thereof
Step 4
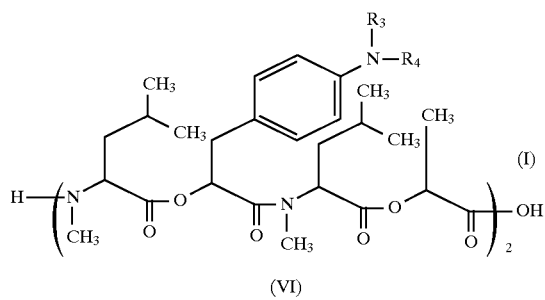
(VI)
or a reactive derivative of the amino or carboxyl group thereof, or a salt thereof
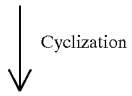 Cyclization
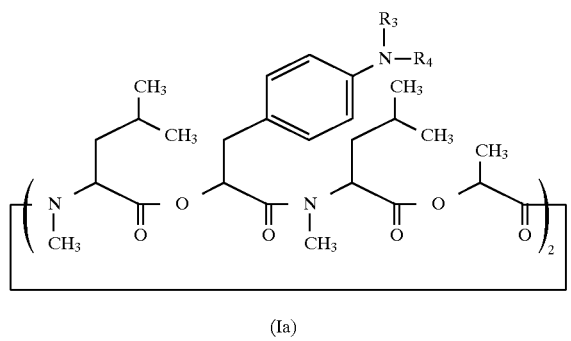
(Ia)
or a salt thereof Step 5

Removal of the amino-protecting group

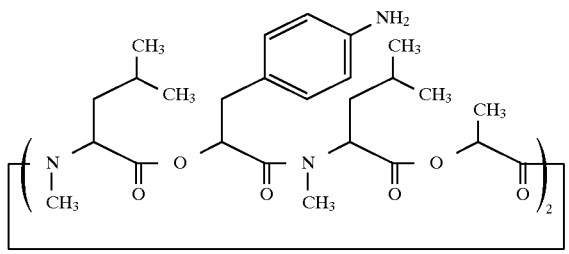

(Ib)

or a salt thereof

Step 6

$(XCH_2CH_2)_2O$
(VII)

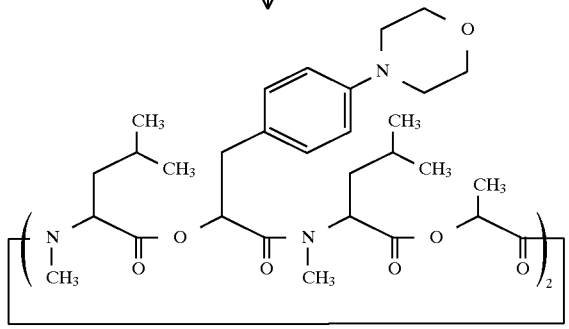

(I)

or a salt thereof (In the above reaction schema, $R_1$ represents hydrogen or an amino-protecting group; $R_2$ represents carboxy or protected carboxy; $R_3$ and $R_4$ independently represent hydrogen, lower alkyl, or an amino-protecting group, provided that at least either $R_3$ or $R_4$ represents an amino-protecting group; X represents a leaving group).

In the above reaction schema, compounds (Ia) and compound (IV) are novel substances.

Throughout this specification, amino acids, peptides, protective groups, condensing agents, etc. are indicated by the abbreviations adopted by IUPAC-IUB (the Commission on the Nomenclature of Organic Chemistry), which are conventionally used in the art.

Moreover, the amino acids and their residues as represented by such abbreviations are L-configured unless otherwise specified, and any D-configured compound or residue is indicated by the prefix D-.

The abbreviations used in connection with this invention are as follows.

Boc: t-butoxycarbonyl
Bzl: benzyl
Lac: 2-hydroxypropionic acid (lactic acid)
MeLeu: methylleucine
p-CbmNHPhLac: 2-hydroxy-3-(4-methoxycarbonylaminophenyl)propionic acid [β-(p-methoxycarbonylaminophenyl)lactic acid]

p-MorPhLac: 2-hydroxy-3-(4-morpholinophenyl)propionic acid [β-(p-morpholinophenyl)lactic acid]
P-NH₂PhLac: 3-(4-aminophenyl)-2-hydroxypropionic acid [β-(p-aminophenyl)lactic acid]
Ms: methanesulfonic acid The preferred salt of any of compounds (I), (Ia), (Ib), (II), (III), (IV), (V), and (VI) includes nontoxic salts of the common kinds, namely salts with bases and acid addition salts. To be more specific, there can be mentioned alkali metal salts (e.g. sodium salt, potassium salt, cesium salt, etc.), alkaline earth metal salts (e.g. calcium salt, magnesium salt, etc.), salts with inorganic bases such as ammonium salt, salts with organic bases such as organic amines (e.g. triethylamine salt, pyridine salt, picoline salt, ethanolamine salt, triethanolamine salt, dicyclohexylamine salt, N,N'-dibenzylethylenediamine salt, etc.), inorganic acid addition salts (e.g. hydrochloride, hydrobromide, sulfate, phosphate, etc.), organic carboxylic acid addition salts or organic sulfonic acid addition salts (e.g. formate, acetate, trifluoroacetate, maleate, tartrate, methanesulfonate, benzenesulfonate, p-toluenesulfonate, etc.), and salts with basic or acidic amino acids (e.g. arginate, aspartate, glutamate, etc.).

The preferred examples as well as paraphrases of various terms defining this invention as used hereinbefore and after in this specification are now presented.

The term "lower" means that the number of constituent carbon atoms is within the range of 1–6, inclusive, preferably 1–4, unless otherwise indicated.

The preferred "leaving group" includes halogen, such as fluorine, chlorine, bromine, or iodine, alkylsulfonic esters such as methanesulfonic ester, and arylsulfonic esters such as p-toluenesulfonic ester.

The preferred "protected carboxy" is "esterified carboxy", which includes lower alkyl esters optionally having one or more suitable substituents. For example, there can be mentioned lower alkyl esters (lower alkoxycarbonyl groups) such as methyl ester, ethyl ester, propyl ester, isopropyl ester, butyl ester, isobutyl ester, tert-butyl ester, pentyl ester, tert-pentyl ester, hexyl ester, etc.; lower alkanoyloxy-lower alkyl esters (lower alkanoyloxy-lower alkoxycarbonyl groups) such as acetoxymethyl ester, propionyloxymethyl ester, butyryloxymethyl ester, valeryloxymethyl ester, pivaloyloxymethyl ester, hexanoyloxymethyl ester, etc.; mono- (or di- or tri-) halo(lower)alkyl esters (mono-(or di- or tri-)halo(lower)alkoxycarbonyl groups) such as 2-iodoethyl ester, 2,2,2-trichloroethyl ester, etc.; lower alkenyl esters (lower alkenyloxycarbonyl groups) such as vinyl ester, allyl ester, etc.; and ar(lower)alkyl esters (ar(lower) alkoxycarbonyl groups) optionally having 1 or more substituents, such as benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc. Particularly preferred, among them, are lower alkyl esters (lower alkoxycarbonyl groups) and ar(lower) alkyl esters (ar(lower)alkoxycarbonyl groups). The most preferred are butyl ester (butoxycarbonyl) and benzyl ester (benzyloxycarbonyl).

The protective group of said protected carboxy includes those protective groups for temporary protection of the carboxyl function which are routinely used in the field of amino acid and peptide chemistry.

The preferred "amino-protecting group" includes various acyl groups, e.g. lower alkanoyl such as formyl, acetyl, propionyl, butyryl, isobutyryl, valeryl, isovaleryl, pivaloyl, hexanoyl, etc; mono-(or di- or tri-)-halo(lower)alkanoyl such as chloroacetyl, bromoacetyl, dichloroacetyl, trifluoroacetyl, etc.; lower alkoxycarbonyl such as methoxycarbonyl, ethoxycarbonyl, propoxycarbonyl, isopropoxycarbonyl, butoxycarbonyl, tert-butoxycarbonyl, pentyloxycarbonyl, tert-pentyloxycarbonyl, hexyloxycarbonyl, etc.; carbamoyl; aroyl such as benzoyl, toluoyl, naphthoyl, etc.; ar(lower)alkanoyl such as phenylacetyl, phenylpropionyl, etc.; aryloxycarbonyl such as phenoxycarbonyl, naphthyloxycarbonyl, etc.; aryloxy (lower)alkanoyl such as phenoxyacetyl, phenoxypropionyl, etc.; arylglyoxyloyl such as phenylglyoxyloyl, naphthylglyoxyloyl, etc.; ar(lower)alkoxycarbonyl optionally having a suitable substituent, such as benzyloxycarbonyl, phenethyloxycarbonyl, p-nitrobenzyloxycarbonyl, etc.; substituted or unsubstituted ar(lower)alkylidene groups such as benzylidene, hydroxybenzylidene, etc.; and ar(lower)alkyl such as mono- (or di- or tri-)phenyl(lower)alkyl groups such as benzyl, phenethyl, benzhydryl, trityl, etc. Preferred are lower alkoxycarbonyl groups. The most preferred for $R_1$ in the above formula is t-butoxycarbonyl and the most preferred for $R_3$ or $R_4$ in the same formula is methoxycarbonyl.

The amino-protecting group mentioned above includes those protective groups for temporary protection of the amino function which are conventionally used in the field of amino acid and peptide chemistry.

[0020]

The process for production of the objective compound (I) is now described in detail.

Production Process

Step 1

Compound (IV) or a salt thereof can be produced by reacting compound (II) or a reactive derivative of the carboxyl group thereof, or a salt thereof, with compound (III) or a reactive derivative of the amino group thereof, or a salt thereof.

This reaction can be carried out according to the conventional procedure for transforming a carboxyl group into an amide.

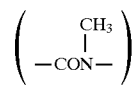

The preferred reactive derivative of the carboxyl group of compound (II) includes the acid halide, acid anhydride, active amide, and active ester. The preferred examples are the acid chloride; acid azide; mixed acid anhydrides with various acids such as substituted phosphoric acids (e.g. dialkylphosphoric acid, phenylphosphoric acid, diphenylphosphoric acid, dibenzylphosphoric acid, halophosphoric acids, etc.), dialkylphosphorous acids, sulfurous acid, thiosulfuric acid, sulfuric acid, alkylcarbonic acids, lower alkanesulfonic acids (e.g. methanesulfonic acid, ethanesulfonic acid, etc.), aliphatic carboxylic acids (e.g. acetic acid, propionic acid, butyric acid, isobutyric acid, pivalic acid, pentanoic acid, isopentanoic acid, 2-ethylbutyric acid, trichloroacetic acid, etc.), and aromatic carboxylic acids (e.g. benzoic acid etc.); symmetric acid anhydride; active amides with imidazole, 4-substituted imidazoles, dimethylpyrazole, triazole, tetrazole, etc.; active esters (e.g. cyanomethyl ester, methoxymethyl ester, dimethyliminomethyl [$(CH_3)_2N=CH—$] ester, vinyl ester, propargyl ester, p-nitrophenyl ester, 2,4-dinitrophenyl ester, trichlorophenyl ester, pentachlorophenyl ester, pentafluorophenyl ester, mesylphenyl ester, phenylazophenyl ester, phenylthio ester, p-nitrophenylthio ester, p-cresylthio ester, carboxymethylthio ester, pyranyl ester, pyridyl ester, piperidyl ester, 8-quinolylthio ester, etc.; and esters with N-hydroxy compounds (e.g. N,N-dimethylhydroxylamine, 1-hydroxy-2-(1H)-pyridone, N-hydroxysuccinimide, N-hydroxyphthalimide, 1-hydroxy-1H-benzotriazole, etc.). Those reactive derivatives can be selectively used according to the species of compound (II).

The preferred reactive derivative of the amino group of compound (III) includes the Schiff's base type imino compounds or the corresponding enamine forms, which are available on reaction of compound (III) with carbonyl compounds such as aldehydes or ketones; the silyl derivatives available on reaction of compound (III) with silyl compounds such as bis(trimethylsilyl)acetamide, mono (trimethylsilyl)acetamide, bis(trimethylsilyl)urea, etc.; and the derivatives available on reaction of compound (III) with phosphorus trichloride or phosgene.

This reaction is generally conducted in the common solvent, such as water, alcohols (e.g. methanol, ethanol, etc.), acetone, dioxane, tetrahydrofuran, acetonitrile, chloroform, methylene chloride, ethylene chloride, ethyl acetate, N,N-dimethylformamide, pyridine, etc., or in an organic solvent other than the above that does not interfere with the reaction. Among those solvents, hydrophilic solvents can be used in admixture with water.

The reaction temperature is not so critical but the reaction is generally conducted under cooling, at room temperature or under warming.

When this reaction is carried out using compound (II) as the free acid or in the form of a salt, it is preferable to conduct the reaction in the presence of a conventional condensing agent. The condensing agent includes but is not limited to carbodiimides inclusive of their salts (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide or its hydrochloride, diphenylphosphoryl azide, diethylphosphoryl cyanide, bis(2-oxo-3-oxazolidinyl) phosphinic chloride, etc.); triazoles (e.g. 1-(p-chlorobenzenesulfonyloxy)-6-chloro-1H-benzotriazole, N-hydroxybenzotriazole, etc.); imidazoles (e.g. N,N'-carbonyldiimidazole, N,N'-carbonylbis(2-methylimidazole), etc.); ketimines (e.g. pentamethyleneketene-N-cyclohexylimine, diphenylketene-N-cyclohexylimine, etc.); ethoxyacetylene; 1-alkoxy-1-chloroethylenes; trialkyl phosphites; ethyl polyphosphate; isopropyl polyphosphate; phosphorus oxychloride (phosphoryl chloride); diphenylphosphoryl chloride; triphenylphosphine; phosphorus trichloride, thionyl chloride; oxalyl chloride; halopyridinium salts (e.g. 2-chloro-1-methylpyridinium iodide etc.); cyanuric chloride; lower alkyl haloformates (e.g. ethyl chloroformate, isopropyl chloroformate, etc.); 2-ethyl-7-hydroxybenzisoxazolium salts; 2-ethyl-5-(m-sulfophenyl)isoxazolium hydroxide inner salt; and Vilsmeier's reagents prepared by reacting N,N-dimethylformamide with thionyl chloride, phosgene, trichloromethyl chloroformate, phosphorus oxychloride, or the like.

This reaction can be carried out in the presence of an inorganic or organic base such as alkali metal hydroxides (e.g. sodium hydroxide, potassium hydroxide, etc.), alkali metal carbonates (e.g. sodium carbonate, potassium carbonate, etc.), alkali metal hydrogencarbonates (e.g. sodium hydrogencarbonate, potassium hydrogencarbonate, etc.), tri(lower)alkylamines (e.g. trimethylamine, triethylamine, etc.), pyridine or its derivatives (e.g. picoline, lutidine, 4-dimethylaminopyridine, etc.), N-(lower)alkylmorpholines (e.g. N-methylmorpholine etc.), and N,N-di(lower)alkylbenzylamines, among other bases.

Step 2

Compound (V) or a salt thereof can be produced by subjecting compound (IV) or a salt thereof to a reaction for elimination of the carboxy-protecting group.

This reaction is carried out by the conventional procedure for hydrolytic or reductive removal of a carboxy-protecting group.

The hydrolysis reaction is preferably carried out in the presence of a base or an acid (inclusive of a Lewis acid).

The preferred base includes both inorganic and organic bases, for example alkali metals (e.g. sodium, potassium, etc.), alkaline earth metals (e.g. magnesium, calcium, etc.), hydroxides, carbonates or hydrogencarbonates of said metals, alkali metal alkoxides (e.g. sodium methoxide, sodium ethoxide, potassium t-butoxide, etc.), alkali metal acetates, alkaline earth metal phosphates, alkali metal hydrogen phosphates (e.g. disodium hydrogen phosphate, dipotassium hydrogen phosphate, etc.), tri(lower)alkylamines (e.g. trimethylamine, triethylamine, etc.), pyridine or its derivatives (e.g. picoline, lutidine, 4-dimethylaminopyridine, etc.), N-(lower)alkylmorpholine (e.g. N-methylmorpholine etc.), 1,5-diazabicyclo[4.3.0]non-5-ene, 1,4-diazabicyclo[2.2.2]octane, 1,8-diazabicyclo[5.4.0]undec-7-ene, quinoline, and so forth.

The preferred acid includes organic acids (e.g. formic acid, acetic acid, propionic acid, trichloroacetic acid, trifluoroacetic acid, etc.) and inorganic acids (e.g. hydrochloric acid, hydrobromic acid, sulfuric acid, etc.). The deprotection reaction using a trihaloacetic acid (e.g. trichloroacetic acid, trifluoroacetic acid, etc.) can be hastened by adding a cation acceptor (e.g. phenol, anisole, etc.).

This hydrolysis reaction is generally conducted in the common solvent such as water, alcohol (e.g. methanol, ethanol, etc.), diethyl ether, dioxane, tetrahydrofuran, methylene chloride, ethyl acetate, acetic acid or the like, a mixture of such common solvents, or an organic solvent other than the common solvent that does not adversely affect the reaction. Where the above-mentioned base or acid is a liquid, it can also be used as the solvent.

The reaction temperature is not so critical but the reaction is generally carried out under cooling, at room temperature, or under warming.

The reductive deprotection reaction can be carried out by chemical reduction or by catalytic reduction.

The preferred reducing agent for chemical reduction includes various combinations of metals (e.g. tin, zinc, iron, etc.) or metal compounds (e.g. chromium chloride, chromium acetate, etc.) with organic or inorganic acids (e.g. formic acid, acetic acid, propionic acid, trifluoroacetic acid, p-toluenesulfonic acid, hydrochloric acid, hydrobromic acid, etc.).

The preferred catalyst for catalytic reduction includes the common catalysts, for example platinum catalysts (e.g. platinum plate, platinum sponge, platinum black, colloidal platinum, platinum oxide, platinum wire, etc.), palladium catalysts (e.g. palladium sponge, palladium black, colloidal palladium, palladium oxide, palladium-on-carbon, palladium-on-barium sulfate, palladium-on-barium carbonate, etc.), nickel catalysts (e.g. reducing nickel, nickel oxide, Raney nickel, etc.), cobalt catalysts (e.g. reducing cobalt, Raney cobalt, etc.), iron catalysts (e.g. reducing iron, Raney iron, etc.), and copper catalysts (e.g. reducing copper, Raney copper, Ullmann copper, etc.).

The reduction reaction is generally conducted in a solvent which does not interfere with the reaction, such as water, alcohols (e.g. methanol, ethanol, propanol, etc.), N,N-dimethylformamide, etc., or a mixture of such solvents. Where the above-mentioned acid for chemical reduction is a liquid, it can be used as the solvent. The preferred solvent for catalytic reduction includes not only the above-mentioned solvents but also the common solvents such as diethyl ether, dioxane, tetrahydrofuran, etc. and mixtures of such solvents.

The reaction temperature for this reduction is not so critical but the reaction is generally carried out under cooling, at room temperature, or under warming.

Step 3

Compound (VI) or a salt thereof can be produced by subjecting compound (V) or a salt thereof to a reaction for elimination of the amino-protecting group.

This reaction is carried out in substantially the same manner as Step 2. Therefore, the above description of Step 2 can be referred to for the reaction conditions which can be employed.

Step 4

Compound (Ia) or a salt thereof can be produced by subjecting compound (VI) or a reactive derivative of the amino or carboxyl group thereof, or a salt thereof, to cyclization reaction.

The reactive derivative of the amino group of compound (VI) is preferably selected from among the derivatives mentioned for Step 1.

The preferred reactive derivative of the carboxyl group of compound (VI) is also preferably selected from among the derivatives mentioned for Step 1.

This reaction is carried out by the conventional cyclization procedure, for example under heating or in the presence of a condensing agent. The preferred condensing agent can be selected from among the condensing agents mentioned for Step 1.

This reaction can also be conducted in the presence of an inorganic or organic base such as alkali metal hydroxides (e.g. sodium hydroxide, potassium hydroxide, etc.), alkali metal carbonates (e.g. sodium carbonate, potassium carbonate, etc.), alkali metal hydrogencarbonates (e.g. sodium hydrogencarbonate, potassium hydrogencarbonate, etc.), tri(lower)alkylamines (e.g. trimethylamine, triethylamine, etc.), pyridine or its derivatives (e.g. picoline, lutidine, 4-dimethylaminopyridine, etc.), N-(lower) alkylmorpholines (e.g. N-methylmorpholine etc.), and N,N-di(lower)alkylbenzylamines, among other bases.

The reaction in the presence of a condensing agent is generally carried out in the common solvent, such as alcohol (e.g. methanol, ethanol, propanol, etc.), acetonitrile, pyridine, N,N-dimethylformamide, 4-methyl-2-pentanone, tetrahydrofuran, benzene, toluene, xylene, etc., a mixture of such common solvents, or an organic solvent other than said common solvents that does not adversely affect the reaction.

The reaction temperature is not so critical but the reaction is generally carried out under cooling, at room temperature, or under warming.

The cyclization reaction under heating can be carried out in an organic solvent such as that mentioned just above under heating at a temperature below the boiling point of the solvent used.

Step 5

Compound (Ib) or a salt thereof can be produced by subjecting compound (Ia) or a salt thereof to a reaction for elimination of the amino-protecting group.

This reaction can be carried out by using a suitable acid in combination with a liquid acid which can serve as a solvent.

The suitable acid mentioned just above includes but is not limited to hydrochloric acid, hydrobromic acid, and hydroiodic acid.

The preferred liquid acid includes but is not limited to formic acid, acetic acid, propionic acid, methanesulfonic acid, and trifluoromethanesulfonic acid.

The reaction temperature is not so critical but the reaction is generally conducted under cooling, at room temperature, or under warming.

Most preferably, this reaction can be carried out in the presence of hydrogen bromide and acetic acid at a reaction temperature of about 35° C. The concentration of hydrogen bromide is generally 5% through saturation and most preferably about 30%.

Step 6

The objective compound (I) or salt thereof can be produced by reacting compound (Ib) or a salt thereof with compound (VII).

This reaction can be carried by known technology, for example the cyclizing process described in WO 093/19053, that comprises using a compound (VII) having two leaving groups. (chloro in this example) in combination with a suitable base and additive.

The preferred base includes inorganic bases such as potassium carbonate, sodium hydrogencarbonate, cesium carbonate, etc. and organic bases such as triethylamine, pyridine, etc.

The preferred additive may for example be sodium iodide, potassium iodide, or a tetraalkylammonium iodide.

The solvent can be the common organic solvent or a mixture of water with an organic solvent.

The reaction temperature is not so critical but the reaction is generally carried out under cooling, at room temperature, or under warming.

Most preferably, the reaction can be carried out using a system comprising compound (VII) (X=Cl), sodium carbonate, sodium iodide, and acetonitrile at the reflux temperature of acetonitrile.

The compound obtained in each of the above steps can be isolated and purified by the conventional procedures such as extraction, precipitation, fractional crystallization, column chromatography, and recrystallization.

In the synthesis of the objective compound (I) known to have excellent parasiticidal activity and be useful as an anthelmintic for human and animal use, the process of this invention yields novel synthetic intermediates which can be more easily purified than the conventional synthetic intermediates involved in the prior art process. Furthermore, by exploiting the synthesis through those novel intermediates, an industrial production process remarkably improved in the crystallizability and yield of compound (I) can be established as herein disclosed.

The following production examples and working examples are further illustrative of this invention.

Production Example 1

Camphorsulfonic acid (23.8 g) and dimethylaminopyridine (24.9 g) are added to acetonitrile (1.7 l) under ice-cooling and, after complete dissolution, Boc-MeLeu-OH (125.6 g) and H-D-p-CbmNHPhLac-OBzl (182 g) are added under ice-cooling. Then, N,N'-dicyclohexylcarbodiimide (126.8 g) is added and the mixture is stirred at the same temperature for 4 hours. The precipitated dicyclohexylurea is then filtered off and the solvent is distilled off. The residue is diluted with diisopropyl ether (5 l) and washed serially with 5% aqueous solution of sodium hydrogencarbonate (1.7 l), water (0.9 l), 5% aqueous solution of citric acid (1.7 l), water (0.9 l), and saturated aqueous solution of sodium chloride (1.0 l). Then, acetic acid (20 ml) and methanol (15 ml) are added and the mixture is stirred at room temperature for 15 hours. The precipitated byproduct dicyclohexylurea is filtered off and the diisopropyl ether solution is washed serially with 5% aqueous solution of sodium hydrogencarbonate (1.7 l), water (0.9 l), and saturated aqueous solution of sodium chloride (1.0 l) and dried over anhydrous sodium sulfate (700 g). The solvent is then distilled off to provide Boc-MeLeu-D-p-CbmNHPhLac-OBzl (282.05 g).

NMR (CDCl$_3$, δ): 0.90 (6H, d), 1.4–1.65 (12H, m), 2.63 (s) & 2.65 (s) (3H), 3.05–3.15 (2H, m), 3.76 (3H, s), 4.65–4.75 (m) & 4.95–5.25 (m) (4H), 6.73 (1H, br s), 7.08 (2H, d), 7.2–7.4 (7H, m).

Production Example 2

To a solution of Boc-MeLeu-D-p-CbmNHPhLac-OBzl (223.25 g) in methanol (1.26 l) are added 10% palladium-on-carbon (wet, 41.5 g) and ammonium formate (52.8 g) in a nitrogen atmosphere at room temperature and the mixture is stirred for 45 minutes. This mixture is filtered through Celite to remove the palladium-on-carbon and the Celite is washed with methanol (1.2 l). The solvent is then distilled off and the residue is diluted with 5% aqueous solution of potassium hydrogensulfate (1.7 l) and ethyl acetate (1.7 l). The organic layer is separated and the aqueous layer is extracted with ethyl acetate (0.87 l) and ethyl acetate (0.7 l). The organic layers are combined and washed serially with 5% aqueous solution of potassium hydrogensulfate (1.0 l), water (1.0 l), and saturated aqueous solution of sodium chloride (0.7 l) and dried over anhydrous sodium sulfate (700 g). The solvent is then distilled off to provide Boc-MeLeu-D-p-CbmNHPhLac-OH (208.15 g).

NMR (CDCl$_3$, $\delta$): 0.81–0.95 (6H, m), 1.19–1.80 (12H, m), 2.72 (s) & 2.77 (s) (3H), 3.05–3.28 (2H, m), 3.77 (3H, s), 4.60–4.75 (1H, m), 5.18–5.35 (1H, m), 5.45–5.75 (1H, m), 6.82–7.03 (1H, m), 7.14 (2H, d), 7.30 (2H, d).

Production Example 3

A decompressible 3-necked flask equipped with a thermometer and a Dean-Stark trap is charged with 85% aqueous solution of lactic acid (127.12 g), benzyl alcohol (260.8 ml), toluene (1.2 l), and p-toluenesulfonic acid monohydrate (45.65 g). In an oil bath maintained at 80° C. and under decompression (>200 mmHg) so as to reflux the system at an internal temperature between 60° and 65° C., the reaction mixture is heated with continuous removal of water for 3 hours and a half. After the reaction mixture is cooled to room temperature, 5% aqueous solution of sodium hydrogencarbonate (400 ml) is added cautiously. The organic layer is separated, washed serially with 5% aqueous solution of sodium hydrogencarbonate (400 ml), 5% aqueous solution of citric acid (400 ml), and saturated aqueous solution of sodium chloride (400 ml) and dried over anhydrous sodium sulfate. The organic solvent is then distilled off. The residue is diluted with quinoline (190 ml) and distilled to recover a fraction boiling at 94°–112° C./1.5 mmHg (177.92 g). This fraction is diluted with diisopropyl ether (0.5 l) and the dilution is washed serially with 5% aqueous solution of citric acid (200 ml) twice and saturated aqueous solution of sodium chloride (200 ml) and dried over anhydrous sodium sulfate. The organic layer is then distilled off to provide H-L-Lac-OBzl (153.27 g).

NMR (CDCl$_3$, $\delta$): 1.44 (3H, d), 2.75–2.90 (1H, m), 4.23–4.40 (1H, m), 5.21 (2H, s), 7.3–7.45 (5H, m).

Production Example 4

To a solution of H-L-Lac-OBzl (153.27 g) in N,N-dimethylformamide (1.27 l) is added triethylamine (177 ml), and methanesulfonyl chloride (145.48 g) is added dropwise over 100 minutes under ice-cooling. This reaction mixture is poured in water (6.4 l) and extracted with diisopropyl ether (1.8 l) and further with two portions of diisopropyl ether (0.6 l each). The organic layers were combined, washed serially with 5% aqueous solution of sodium hydrogencarbonate (850 ml) twice, 5% aqueous solution of citric acid (850 ml), and saturated aqueous solution of sodium chloride (850 ml), and dried over anhydrous sodium sulfate. The organic solvent is then distilled off to provide Ms-L-Lac-OBzl (171.8 g).

NMR (CDCl$_3$, $\delta$): 1.64 (3H, d), 3.09 (3H, s), 5.10–5.28 (3H, m), 7.30–7.45 (5H, m).

Production Example 5

To a solution of Boc-MeLeu-OH (108.52 g) in N,N-dimethylformamide (331 ml) is added cesium carbonate (79.2 g), and the mixture is stirred at room temperature for one hour and a half. To the resulting suspension is added a solution of Ms-L-Lac-OBzl (171.4 g) in N,N-dimethylformamide (111 ml), and the mixture is stirred at room temperature for 20 hours. This reaction mixture is diluted with water (2.2 l) and extracted with diisopropyl ether (1.1 l) once and further with two portions of diisopropyl ether (0.55 l each) . The organic layers are combined, washed serially with 5% aqueous solution of sodium hydrogencarbonate (1.1 l), 5% aqueous solution of citric acid (1.1 l), and saturated aqueous solution of sodium chloride (1.1 l), and dried over anhydrous sodium sulfate. The organic solvent is then distilled off.

To this residue (esterification product) is added 4N-HCl/ethyl acetate (1.66 l) under ice-cooling, and the mixture is stirred at that temperature for one hour and a half, after which the solvent is distilled off. To the residue is added 0.1N-hydrochloric acid (4.4 l) and the mixture is washed with diisopropyl ether (2.2 l) and further with two portions of diisopropyl ether (1.1 l each). After addition of diisopropyl ether (2.2 l) to the aqueous layer, sodium hydrogencarbonate is added with stirring until the pH is brought to 8–9 and the organic layer is separated. The aqueous layer is further extracted with two portions of diisopropyl ether (2.2 l each). The organic layers are combined, washed serially with two portions of 5% aqueous solution of sodium hydrogencarbonate (1.1 l each) and saturated aqueous solution of sodium chloride (1.1 l) and dried over anhydrous sodium sulfate. The organic solvent is then distilled off to provide H-MeLeu-D-Lac-OBzl (130.5 g).

NMR (CDCl$_3$, $\delta$): 0.90 (3H, d), 0.94 (3H, d), 1.30–1.58 (5H, m), 1.62–1.82 (1H, m), 2.34 (3H, s), 3.26 (1H, t), 5.10–5.22 (3H, m), 7.28–7.45 (5H, m).

Production Example 6

To a solution of Boc-MeLeu-D-p-CbmNHPhLac-OH (179.4 g) and H-MeLeu-D-Lac-OBzl (124.3 g) in acetonitrile (1.93 l) is added N-methylmorpholine (101.6 ml) under ice-cooling, and then at an internal temperature of 4°–5° C., diphenylphosphoryl chloride ((PhO)$_2$P(O)Cl 95.8 ml) is added dropwise over about one hour. The mixture is then stirred at the same temperature for 2 hours and 40 minutes. After the resulting crystals are filtered off, the solvent is distilled off. To the residue are added water (2.7 l) and ethyl acetate (2.7 l), and after the mixture is allowed to stand, the organic layer is separated. The aqueous layer is extracted with ethyl acetate (2.0 l) and further with ethyl acetate (1.6 l). The organic layers are combined, washed serially with 5% aqueous solution of potassium hydrogensulfate (1.6 l), water (1.1 l), 5% aqueous solution of sodium hydrogencarbonate (1.6 l), water (1.1 l), and saturated aqueous solution of sodium chloride (1.1 l), and dried over anhydrous sodium sulfate (1 kg). The solvent is then distilled off to provide Boc-MeLeu-D-p-CbmNHPhLac-MeLeu-D-Lac-OBzl (306.7 g).

NMR (CDCl$_3$, $\delta$): 0.82–1.00 (12H, m), 1.40–1.80 (18H, m), 2.72–2.95 (6H, m), 3.05–3.15 (2H, m), 3.77 (3H, s), 4.60–4.80 (m) & 4.90–5.45 (m) (6H), 6.60 (1H br s), 7.13–7.40 (9H, m).

Production Example 7

To a solution of Boc-MeLeu-D-p-CbmNHPhLac-MeLeu-D-Lac-OBzl (146.6 g) in methanol (0.58 l) are added 10% palladium-on-carbon (wet, 19.2 g) and ammonium formate (24.5 g) in a nitrogen atmosphere at room temperature and the mixture is stirred for 35 minutes. This reaction mixture is filtered through Celite to remove the palladium-on-carbon and the Celite is washed with methanol (0.5 l). The solvent is then distilled off. To the residue are added 5% aqueous solution of potassium hydrogensulfate (1 l) and ethyl acetate (1 l), and the organic layer is separated. The aqueous layer is extracted with ethyl acetate (0.6 l) and further with ethyl acetate (0.5 l). The organic layers are combined, washed serially with 5% aqueous solution of potassium hydrogensulfate (0.63 l), water (0.63 l) and saturated aqueous solution of sodium chloride (0.5 l) and dried over anhydrous sodium sulfate (400 g). The solvent is then distilled off to provide Boc-MeLeu-D-p-CbmNHPhLac-MeLeu-D-Lac-OH (134.41 g)

NMR (CDCl$_3$, δ): 0.82–1.00 (12H, m), 1.39–1.80 (18H, m), 2.72–3.20 (8H, m), 3.77 (3H, s), 4.62–5.78 (4H, m), 6.25–6.45 (1H, m), 6.72–6.85 (1H, m), 7.16 (2H, d), 7.29 (2H, d).

Production Example 8

To Boc-MeLeu-D-p-CbmNHPhLac-MeLeu-D-Lac-OBzl (160 g) is added 4N-HCl/ethyl acetate (0.483 l) at room temperature and the mixture is stirred for 30 minutes. The solvent is then distilled off. The residue is diluted with water (0.965 l) and ethyl acetate (0.48 l) and sodium carbonate is added until the pH is brought to 8–9. The mixture is allowed to stand and the organic layer is separated. The aqueous layer is further extracted with ethyl acetate (0.24 l). The organic layers are combined, washed with 5% aqueous solution of sodium hydrogencarbonate (0.48 l), water (0.48 l) and saturated aqueous solution of sodium chloride (1.1 l) in the order mentioned, and dried over anhydrous sodium sulfate (500 g). The organic solvent is then distilled off to provide H-MeLeu-D-p-CbmNHPhLac-MeLeu-D-Lac-OBzl (141.21 g).

NMR (CDCl$_3$, δ): 0.75–0.99 (12H, m), 1.30–1.80 (9H, m), 2.35 (3H, s), 2.93 (3H, s), 3.05 (2H, d), 3.24 (1H, t), 3.77 (3H, s), 5.04–5.55 (5H, m), 6.64 (1H, br s), 7.18 (2H, d), 7.26–7.40 (7H, m).

EXAMPLE 1

To a solution of Boc-MeLeu-D-p-CbmNHPhLac-MeLeu-D-Lac-OH (134.41 g) and H-MeLeu-D-p-CbmNHPhLac-MeLeu-D-Lac-OBzl (141.21 g) in acetonitrile (0.97 l) is added N-methylmorpholine (51.2 ml) under ice-cooling, and diphenylphosphoryl chloride ((PhO)$_2$P(O)Cl) (62.6 g) is added dropwise over about 35 minutes at an internal temperature of 3°–6° C. The mixture is then stirred at the same temperature for one hour and 15 minutes. Then, N-methylmorpholine (5.12 ml) and diphenylphosphoryl chloride ((PhO)$_2$P(O)Cl) (6.26 g) are further added and the mixture is stirred for 45 minutes. The resulting crystals are filtered off and the solvent is distilled to remove the solvent. The residue is diluted with water (2.3 l) and ethyl acetate (2.3 l) and the organic layer available on standing is separated. The aqueous layer is further extracted with ethyl acetate (1.7 l) and again with ethyl acetate (1.3 l). The organic layers are combined, washed with 5% aqueous solution of potassium hydrogensulfate (1.3 l), water (0.9 l), 5% aqueous solution of sodium hydrogen-carbonate (1.3 l), water (0.9 l), and saturated aqueous solution of sodium chloride (0.9 l) in the order mentioned and dried over anhydrous sodium sulfate (0.8 Kg). The solvent is then distilled off to provide Boc-MeLeu-D-p-CbmNHPhLac-MeLeu-D-Lac-MeLeu-D-p-CbmNHPhLac-MeLeu-D-Lac-OBzl (269.15 g).

NMR (CDCl$_3$, δ): 0.80–1.05 (24H, m), 1.15–1.80 (27H, m), 2.72–3.18 (16H, m), 3.77 (6H, s), 5.05–5.52 (10H, m), 6.66 (2H, br s), 7.10–7.33 (13H, m).

EXAMPLE 2

To a solution of Boc-MeLeu-D-p-CbmNHPhLac-MeLeu-D-Lac-MeLeu-D-p-CbmNHPhLac-MeLeu-D-Lac-OBzl (269 g) in methanol (0.8 l) are added 10% palladium-on-carbon (wet, 19.2 g) and ammonium formate (24.5 g) in a nitrogen atmosphere at room temperature, and the mixture is stirred for 40 minutes. This reaction mixture is filtered through Celite to remove the palladium-on-carbon and the Celite is washed with methanol (0.6 l). The solvent is then distilled off. To the residue are added 5% aqueous solution of potassium hydrogensulfate (1.8 l) and ethyl acetate (1.8 l), and the organic layer available on standing is separated. The aqueous layer is further extracted with ethyl acetate (1.0 l) and ethyl acetate (0.5 l). The organic layers are combined, washed serially with 5% aqueous solution of potassium hydrogensulfate (1 l), water (1 l), and saturated aqueous solution of sodium chloride (0.8 l) and dried over anhydrous sodium sulfate (700 g). The solvent is then distilled off to provide Boc-MeLeu-D-p-CbmNHPhLac-MeLeu-D-Lac-MeLeu-D-p-CbmNHPhLac-MeLeu-D-Lac-OH (250.35 g).

NMR (CDCl$_3$, δ): 0.80–1.10 (24H, m), 1.35–1.80 (27H, m), 2.72–3.18 (16H, m), 3.76 (6H, s), 4.60–5.65 (8H, m), 6.75–7.40 (10H, m).

EXAMPLE 3

To Boc-MeLeu-D-p-CbmNHPhLac-MeLeu-D-Lac-MeLeu-D-p-CbmNHPhLac-MeLeu-D-Lac-OH (250.3 g) is added 4N-HCl/ethyl acetate (0.483 l) at room temperature, and after 30 minutes of stirring, the solvent is distilled off. The residue is diluted with ethyl acetate (0.3 l) and toluene (0.3 l) and the solvent is distilled off. The above procedure is repeated for a second time to provide HCl. H-MeLeu-D-p-CbmNHPhLac-MeLeu-D-Lac-MeLeu-D-p-CbmNHPhLac-MeLeu-D-Lac-OH (270.3 g).

NMR (CDCl$_3$, δ): 0.72–1.00 (24H, m), 1.15–1.90 (18H, m), 2.50–3.20 (16H, m), 3.76 (6H, s), 3.70–3.85 (1H, m), 4.95–5.72 (7H, m), 7.00–7.55 (10H, m).

EXAMPLE 4

A solution of HCl. H-MeLeu-D-p-CbmNHPhLac-MeLeu-D-Lac-MeLeu-D-p-CbmNHPhLac-MeLeu-D-Lac-OH (270 g) in tetrahydrofuran (1 l) is added dropwise, under ice-cooling, to N-methylmorpholine (78.4 ml) and diphenylphosphoryl chloride ((PhO)$_2$P(O)Cl) (78.2 g) in tetrahydrofuran (2.88 l) over about 4.5 hours at room temperature, and the mixture is further stirred for 1 hour. To this mixture are added water (4 l) and ethyl acetate (2 l), and the organic layer available on standing is separated. The aqueous layer is further extracted with ethyl acetate (1.5 l) and ethyl acetate (1 l) . The organic layers are combined, washed serially with 5% aqueous solution of potassium hydrogensulfate (2 l), water (1.6 l), 5% aqueous solution of sodium hydrogencarbonate (2 l), water (1.6 l), and saturated aqueous solution of sodium chloride (1.6 l) and dried over anhydrous sodium sulfate (0.8 kg). The solvent is then distilled off to provide crude crystals (215.55 g) of

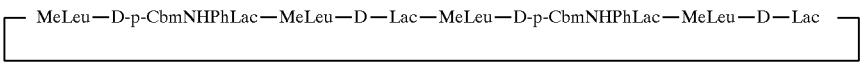

This crude crystal crop is dissolved in ethanol (886 ml) when hot and, then, water (564 ml) is added for precipitation. The resulting crystals are recovered by filtration, washed with ethanol-water (1:1; 400 ml), and dried in vacuo to provide crystals (125.44 g). To this crystal crop is added methanol (1.25 l) and the mixture is refluxed for about 10 minutes. After spontaneous cooling, the insoluble matter is filtered off and the methanol is distilled off. The residue is dissolved in isopropyl alcohol (1.25 l) under heating and the solution is diluted with water (0.5 l) and stirred at room temperature for 2 days. The resulting crystals are collected by filtration, washed with isopropyl alcohol-water (5:2; 0.18 l), and dried in vacuo to provide ⌐ MeLeu—D-p-CbmNHPhLac—MeLeu—D—Lac—MeLeu—D-p-CbmNHPhLac—MeLeu—D—Lac ⌐

(66.6 g)

NMR (CDCl$_3$, δ): 0.80–1.10 (24H, m), 1.20–1.82 (18H, m), 2.70–3.20 (16H, m), 3.77 (6H, s), 4.40–4.55 (m) & 5.05–5.70 (m) (8H), 6.62–6.70 (2H, m), 7.17 (4H, d), 7.32 (4H, d).

EXAMPLE 5

⌐ MeLeu—D-p-CbmNHPhLac—MeLeu—D—Lac—MeLeu—D-p-CbmNHPhLac—MeLeu—D—Lac ⌐

(21.22 g) is added to 30% HBr/acetic acid (96.9 ml) prepared beforehand and the mixture is heated at 35° C. for 3 hours and then stirred at room temperature for a further 14.5 hours. The HBr/acetic acid is distilled off under reduced pressure and the residue is diluted with ethyl acetate (0.4 l) and water (0.4 l). The mixture is adjusted to pH 8 with sodium hydrogencarbonate. The organic layer is separated and the aqueous layer is extracted with ethyl acetate (0.2 l) and ethyl acetate (0.1 l). The organic layers are combined, washed serially with 5% aqueous solution of sodium hydrogencarbonate (0.2 l) and saturated aqueous solution of sodium chloride (0.2 l), and dried over anhydrous sodium sulfate (500 g). The solvent is then distilled off to provide ⌐ MeLeu—D-p-NH$_2$PhLac—MeLeu—D—Lac—MeLeu—D-p-NH$_2$PhLac—MeLeu—D—Lac ⌐

(19.92 g)

NMR (CDCl$_3$, δ): 0.7–1.15 (24H, m), 1.20–1.85 (18H, m), 2.60–3.10 (16H, m), 3.15–3.40 (4H, m), 4.40–4.57 (m) & 5.0–5.70 (m) (8H), 6.60 (4H, d), 7.00 (4H, d).

EXAMPLE 6

A suspension of

⌐ MeLeu—D-p-NH$_2$PhLac—MeLeu—D—Lac—MeLeu—D-p-NH$_2$PhLac—MeLeu—D—Lac ⌐

(19.61 g), sodium carbonate (10.28 g), sodium iodide (7.27 g), and bis(2-chloroethyl) ether (7.01 ml) in acetonitrile is refluxed with stirring for 14 hours. Then, sodium carbonate (0.41 g) and bis(2-chloroethyl) ether (0.28 ml) are further added and the mixture is stirred under reflux for 3 hours. This reaction mixture is diluted with water (0.4 l) and extracted with 3 portions (0.4 l, 0.2 l, and 0.1 l) of ethyl acetate. The organic layers are combined, washed serially with water (0.2 l) and saturated aqueous solution of sodium chloride (0.2 l) and dried over anhydrous sodium sulfate (500 g). The solvent is then distilled off and the residue is dissolved in ethyl acetate (50 ml) prepared beforehand, and the solvent is distilled off. To the residue is added diisopropyl ether (0.1 l), and the mixture is stirred at room temperature for 1 hour. The resulting crystals are recovered by filtration to provide crude crystals (29.25 g) of ┌─ MeLeu—D-p-MorPhLac—MeLeu—D—Lac—MeLeu—D-p-MorPhLac—MeLeu—D—Lac ─┐ hydrochloride.

The crude crystals of

┌─ MeLeu—D-p-MorPhLac—MeLeu—D—Lac—MeLeu—D-p-MorPhLac—MeLeu—D—Lac ─┐ hydrochloride are added to 5% sodium hydrogen-carbonate/water (0.4 l)-ethyl acetate (0.4 l) and the mixture is stirred at room temperature. The organic layer is separated and the aqueous layer is further extracted with ethyl acetate twice (0.2 l×2). The organic layers are combined, washed with 3 portions of 5% aqueous solution of sodium chloride (0.4 l each), dried over anhydrous sodium sulfate (500 g), and passed through a silica gel (38.8 g) column. The solvent is then distilled off under reduced pressure to provide crude crystals (20.33 g) of The above crude crystals of ┌─ MeLeu—D-p-MorPhLac—MeLeu—D—Lac—MeLeu—D-p-MorPhLac—MeLeu—D—Lac ─┐

The above crude crystals of

┌─ MeLeu—D-p-MorPhLac—MeLeu—D—Lac—MeLeu—D-p-MorPhLac—MeLeu—D—Lac ─┐ are dissolved in methanol (200 ml) with heating and after addition of water (60 ml) and spontaneous cooling, the mixture is stirred for about 15 hours. The resulting crystals are collected by filtration and dried in vacuo to recover crystals (17.18 g). The crystals are redissolved in methanol (170 ml) when hot, followed by addition of water (51 ml). After spontaneous cooling, the mixture is stirred for about 15 hours. The crystals which have separated out are collected by filtration and dried in vacuo to provide ┌─ MeLeu—D-p-MorPhLac—MeLeu—D—Lac—MeLeu—D-p-MorPhLac—MeLeu—D—Lac ─┐

(15.83 g)

NMR (CDCl$_3$, δ): 0.70–1.20 (24H, m), 1.20–1.90 (18H, m), 2.62–3.20 (24H, m), 3.70–3.90 (8H, m), 4.4–4.58 (m) & 5.0–5.70 (m) (8H), 6.82 (4H, d), 7.13 (4H, d).

FAB-MS: 1119 (M+H)$^-$

We claim:

1. A compound of the following formula or a salt thereof:

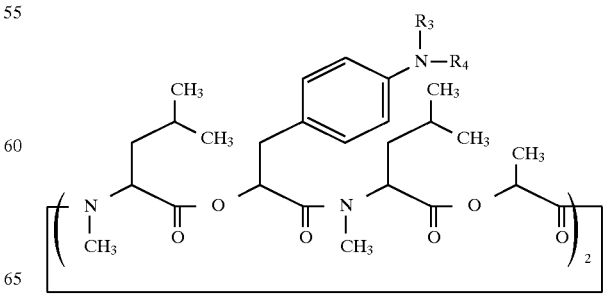

wherein $R_3$ and $R_4$ independently represent hydrogen, lower alkyl, or an amino-protecting group, with at least either $R_3$ or $R_4$ being an amino-protecting group.

2. The compound or its salt according to claim 1 wherein $R_3$ represents hydrogen and $R_4$ represents lower alkoxycarbonyl.

3. The compound or its salt according to claim 1 wherein $R_3$ represents hydrogen and $R_4$ represents methoxycarbonyl.

4. A compound of the following formula or a salt thereof:

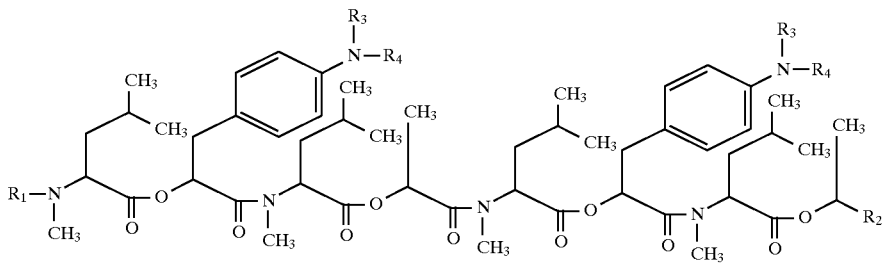

wherein $R_1$ represents hydrogen or an amino-protecting group, $R_2$ represents carboxy or protected carboxy, $R_3$ and $R_4$ independently represent hydrogen, lower alkyl, or an amino-protecting group, with at least either $R_3$ or $R_4$ being an amino-protecting group.

5. The compound or its salt according to claim 4 wherein $R_1$ represents lower alkoxycarbonyl, $R_2$ represents ar(lower)alkoxycarbonyl, $R_3$ represents hydrogen, and $R_4$ represents lower alkoxycarbonyl.

6. The compound or its salt according to claim 4 wherein $R_1$ represents t-butoxycarbonyl, $R_2$ represents benzyloxycarbonyl, $R_3$ represents hydrogen, and $R_4$ represents methoxycarbonyl.

7. The compound or its salt according to claim 4 wherein $R_1$ represents t-butoxycarbonyl, $R_2$ represents carboxy, $R_3$ represents hydrogen, and $R_4$ represents methoxycarbonyl.

8. The compound or its salt according to claim 4 wherein $R_1$ represents hydrogen, $R_2$ represents carboxy, $R_3$ represents hydrogen, and $R_4$ represents methoxycarbonyl.

9. A process for producing a depsipeptide derivative or a salt thereof which comprises subjecting a compound of the formula:

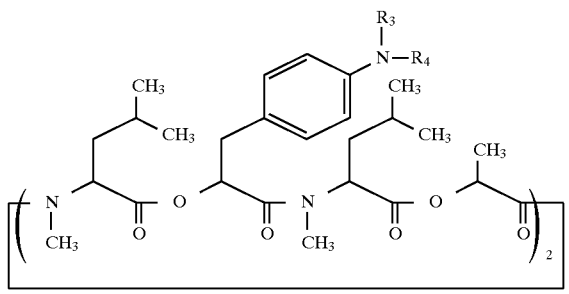

(wherein $R_3$ and $R_4$ independently represent hydrogen, lower alkyl, or an amino-protecting group, with at least either $R_3$ or $R_4$ being an amino-protecting group) or a salt thereof to a deprotection reaction for elimination of the amino-protecting group to provide a compound of the formula:

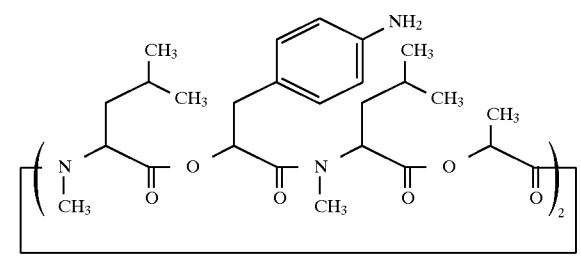

or a salt thereof.

10. A process for producing a depsipeptide derivative or a salt thereof which comprises subjecting a compound of the formula:

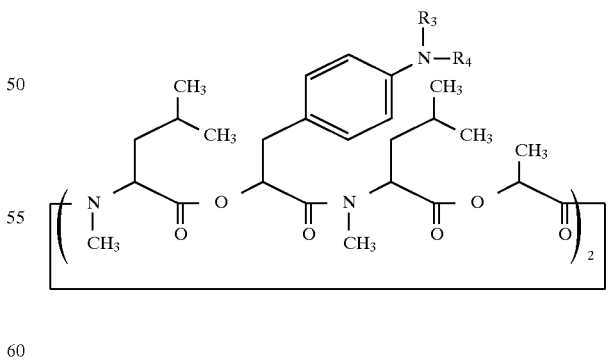

(wherein $R_3$ and $R_4$ independently represent hydrogen, lower alkyl, or an amino-protecting group, with at least either $R_3$ or $R_4$ being an amino-protecting group) or a salt thereof to a deprotection reaction for elimination of the amino-protecting group to provide a compound of the formula:

25
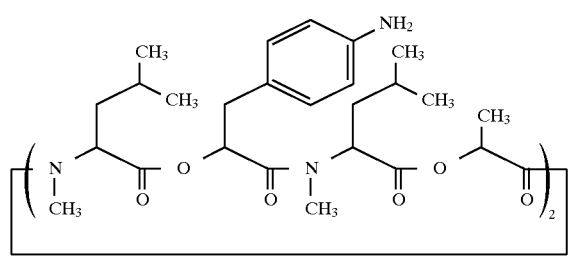
or a salt thereof and reacting the compound or salt thus obtained with a compound of the formula $(XCH_2CH_2)_2O$ (wherein X represents a leaving group) to provide a compound of the formula:
26
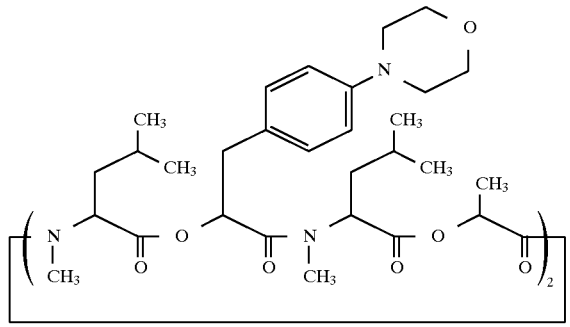
or a salt thereof.
* * * * *